US006255287B1

(12) United States Patent
Watson et al.

(10) Patent No.: US 6,255,287 B1
(45) Date of Patent: Jul. 3, 2001

(54) LIVESTOCK FEEDLOT ADAPTATION TREATMENT METHOD AND PRODUCT

(75) Inventors: Charles Watson; Scott Charles Watson, both of Norfolk; George G. Gentry, Omaha, all of NE (US)

(73) Assignee: Vit-E-Men Co., Inc., Norfolk, NE (US)

( * ) Notice: Subject to any disclaimer, the term of this patent is extended or adjusted under 35 U.S.C. 154(b) by 0 days.

(21) Appl. No.: 08/602,240

(22) Filed: Feb. 16, 1996

Related U.S. Application Data

(63) Continuation of application No. 08/225,797, filed on Apr. 11, 1994, now abandoned, which is a continuation of application No. 08/072,122, filed on Jun. 7, 1993, now abandoned.

(51) Int. Cl.$^7$ .......................... A61K 31/70; A61K 31/28; A61K 31/315; A61K 31/30
(52) U.S. Cl. ........................ 514/23; 514/492; 514/494; 514/499; 514/501; 514/502; 514/724
(58) Field of Search .............................. 574/23, 492, 494, 574/499, 501, 502, 724

(56) References Cited

U.S. PATENT DOCUMENTS

| | | | |
|---|---|---|---|
| 3,275,514 | * 9/1966 | Saltman | 167/68 |
| 4,202,887 | * 5/1980 | Talbot et al. | 426/2 |
| 4,219,572 | * 8/1980 | Jackman | 426/69 |
| 4,382,966 | * 5/1983 | Mickus et al. | 426/69 |
| 4,600,586 | * 7/1986 | Green | 426/2 |
| 4,774,089 | * 9/1988 | Ashmead | 424/157 |
| 4,937,082 | * 6/1990 | Sawhill | 426/69 |
| 4,992,473 | * 2/1991 | Anderson et al. | 514/653 |
| 5,162,369 | * 11/1992 | Ashmead et al. | 514/491 |
| 5,167,957 | * 12/1992 | Webb et al. | 514/2 |

* cited by examiner

Primary Examiner—Raymond Henley, III
(74) Attorney, Agent, or Firm—Zarley, McKee, Thomte, Voorhees & Sease; Dennis L. Thomte

(57) ABSTRACT

A method of preparing a product for treating livestock comprising providing as ingredients molasses, water, ethyl alcohol, chelated minerals, and at least a vitamin mix. The method includes the steps of mixing the ethyl alcohol and water first, then adding each of the remaining ingredients separately to the mixture of ethyl alcohol and water. The composition is then mixed until homogeneous to provide a liquid treatment which, when introduced into livestock, will reduce considerably the length of, and amount of, lot adaptation stress.

11 Claims, No Drawings

LIVESTOCK FEEDLOT ADAPTATION TREATMENT METHOD AND PRODUCT

This is a continuation of application Ser. No. 08/225,797, filed Apr. 11, 1994, now abandoned, which is a continuation of application Ser. No. 08/072,122 filed Jun. 7, 1993, now abandoned.

BACKGROUND OF THE INVENTION

1. Technical Field

This invention relates to a treatment for stress in livestock, and more particularly to a product and method for successfully drenching rumen animals having symptoms of neurological stress, optimum stress or psychological stress caused by such factors as transportation, weather conditions, nutrient imbalance because of ration changes or geographic changes, and working the animals.

2. Description of the Prior Art

The livestock industry of the present day is spread over a vast geographical area, extending literally from coast to coast. Because of this, it is becoming less common to find cattle raising operations and finishing and slaughter processing facilities close to one another. Therefore, transportation of livestock over large distances has become increasingly common. Such transport from one area of the United States to another can often take up to 36 hours, during which time livestock in the vehicle have no way to get water or feed for themselves. This induces great amounts of stress in the livestock.

The net result is that livestock arriving at finishing facilities do so having all degrees of adequate and inadequate nutrition and consequently nutrient levels of the tissues.

Furthermore, this shipping and handling stress comes at a most inopportune time, specifically, during "lot adaptation", the period of least resistance to disease and parasites and the period in the feeding program when the animals are challenged to create an immune response to build immunity to protect them during the remaining feeding period. The end result is that this "lot adaptation" time has the highest incidence of disease and other livestock health problems. There is therefore a need for a livestock treatment product and method which will substantially reduce livestock losses due to problems encountered during this time period.

Additionally, shipping and handling stress can and usually does result in diminished appetite among the transported livestock. As the livestock must eat and drink to replenish lost minerals and energy to successfully combat disease and other such health problems, getting the just-transported livestock to the feed bunk as soon as possible after transport is very important. There is therefore a need for a method and product which will induce livestock to feed as soon as possible following transport. Also, it is important that the livestock replenish the liquids lost during transport, and thus the livestock's thirst must also be stimulated. The quicker the animal recovers from its stress, the quicker the animal may resume feeding and drinking, and thus the animal's susceptibility to disease and parasitical infection may be returned to near-normal levels.

However, merely stimulating the thirst and appetite of the livestock is not always sufficient to prevent the animal from being infected or to reenergize the animal's immune system. For this purpose, there is a need for a treatment product which will replace minerals and vitamins lost by the livestock during transport. However, while the use of both water and fat-soluble vitamins as replacements is fairly well known, it is also understood that replacement of lost minerals by introduction of trace minerals into the livestock is not the most efficient or effective method of replacement of minerals. This is because trace minerals are not easily absorbed by the digestive system of the livestock, in many instances having a bio-availability in the animal's systems of only 15%–20%. However, if instead of trace minerals, amino acid chelated minerals are used, such minerals are absorbed intact via active transportation through the intestine, thus allowing the essential minerals to be used intercellularly as needed in vital metabolic reactions. In many instances, use of an amino acid chelated mineral can increase bio-availability of the mineral to the system of the animal to greater than 90%. There is therefore a need for a treatment product which combines the advantages of vitamin replacement with the absorption advantages of chelated minerals and further includes a stress-reducing element.

Therefore, an object of the present invention is to provide an improved method and product for reducing neurological stress, optimum stress and/or physiological stress in livestock.

Another object of the present invention is to provide a livestock treatment product which will considerably reduce the length of, and amount of, lot adaptation stress.

Another object of the present invention is to provide a livestock treatment product which includes chelated minerals to quickly and efficiently replace minerals lost by livestock during transport.

Another object of the present invention is to provide a method of preparing a livestock treatment product including as major ingredients molasses, water, ethyl alcohol and chelated minerals and as minor ingredients, at least a vitamin mix, wherein the method includes the steps of mixing the ethyl alcohol and water separately, then adding each of the other ingredients to the initial mixture and then mixing until homogeneous.

Another object of the present invention is to provide a method of treating livestock to reduce livestock adaptation stress wherein the method includes the step of administering to livestock a treatment product as described above.

Another object of the present invention is to provide a product for treating livestock which includes ethyl alcohol to reduce stress in livestock.

Finally, an object of the present invention is to provide a method and product for treating stress in livestock which is relatively inexpensive to manufacture and is safe, convenient and effective in use.

SUMMARY OF THE INVENTION

A method of preparing a product for treating livestock comprises mixing ingredients including molasses, water, ethyl alcohol and chelated minerals and at least a vitamin mix. In accordance with the method, the ethyl alcohol and the water are mixed together, after which each of the other ingredients is separately added to the mix. The combination is then mixed until homogenous to provide a liquid treatment, which, when introduced into livestock, will reduce considerably the length of, and amount of, adaptation stress.

The product of the present invention is a generally homogenous mixture of at least the following ingredients: water, ethyl alcohol, molasses, chelated minerals and a vitamin mix. Water makes up about 10%–50% of the mixture by weight, ethyl alcohol makes up about 3%–25% of the mixture by weight, molasses makes up about 20%–65% of the mixture by weight, chelated minerals make up about 1%–10% of the mixture by weight and vitamin mix makes up about 0.01% to 2% of the mixture by weight.

When this product, prepared as previously described, is administered to livestock following arrival of the livestock in a new lot, lot stress is significantly reduced, and the animals are more quickly returned to a state of normalcy, thus reducing the instances of illness and death.

DESCRIPTION OF THE PREFERRED EMBODIMENT

The major ingredients of the product of the present invention are water, ethyl alcohol, molasses, chelated minerals and a vitamin mix. The amount of water in the product may vary from about 10% to about 75% by weight of the composition. The amount of ethyl alcohol may vary from about 3% to about 25% by weight of the composition. The amount of molasses can vary from about 20% to about 65% by weight of the composition. The amount of chelated minerals can vary from about 1% to about 10% by weight of the composition, and the amount of vitamin mix can vary from about .01% to about 2% by weight of the composition.

It is preferred that the molasses be black strap cane molasses, as this type of molasses is an excellent carrier for the other ingredients in the mixture and is also palatable to livestock. While the preferred embodiment of the present invention is described in connection with black strap cane molasses, it is to be understood that various other kinds of molasses may be substituted for the black strap cane molasses used in the present invention. Similarly while any grain alcohol, synthetic ethanol or other alcohol with or without suitable denaturants can be used, it is preferred that ethyl alcohol be used to provide an immediate energy source for the livestock being administered to. An example of a desirable ethyl alcohol is formula SDA (special denatured alcohol) 35-A (Alcohol Tabacco Tax Division, Internal Revenue Service U.S. Treasury Department). Such an ethyl alcohol is the preferred choice as it may be absorbed immediately from the alimentary canal without the necessity of undergoing digestion, thus providing an immediate rich energy source.

The vitamin mix, as is preferred for processing, can be divided into a fat soluble mix portion including such vitamins as A, D and E and a water soluble vitamin portion including such vitamins as thiamin B1, choline, riboflavin B2, niacin, pantothenic acid, pyridoxine B6, folic acid, biotin, and vitamin B12.

An important element of the present invention is that trace minerals are not used, except those occurring naturally in other ingredients of the present composition and possibly selenium. Instead, it is preferred that a selection of chelated minerals be added to the product of the present invention. These include amino acid chelates of zinc, copper, magnesium, potassium and manganese, in addition to other amino acid chelates such as iron, phosphorous and cobalt which may or may not be added to the product of the present invention.

Livestock's supply of minerals may be depleted during transport of the livestock, minerals which are necessary for proper immune system function. Therefore, it is vitally important to replace these minerals as quickly and efficiently as possible. Inorganic trace minerals generally have a bio availability to the livestock of about 17 to 18%. This means that over 80% of the minerals administered to livestock following transport are wasted.

A metal amino acid chelate such as contemplated for use in the present invention is the product resulting from the reaction of a metal ion from a soluble metal salt with amino acids. In such a stable metal amino chelate, the metal or mineral is attached to two amino acids forming low molecular double heterocyclic rings. In this unique chelated state, the metal is protected by the amino acids and is not precipitated as minerals from salts. Therefore, as a stable amino acid chelate, the chelate is not ionized in the gut as trace minerals are, but is absorbed intact via a different pathway.

As long as these amino acid chelates are smaller than dipeptide molecules, the metal or mineral contained within the chelate may be "smuggled" into the intestinal cells as part of dipeptide molecules. As stabilized amino acid chelates enter the lumen they can be absorbed anywhere on the small intestine. Most of this absorption occurs below the pancreatic duct and is completed in the upper third of the small intestine.

The use of such metal amino acid chelates as substitutes for trace minerals used in other livestock treatments has several advantages. Intestinal absorption is more rapid when using amino acid chelates than minerals from salts. Second, the uptake of amino acid chelates is greater because there is no longer the need for a critical environment. Their absorption is not dependent upon the gut. Third, due to the better and more predictive mineral absorption, amino acid chelates produce less intestinal track side effects, such as irritation, constipation, and diarrhea. In fact, absorption of minerals into the animal's blood stream can be increased from two to five times that possible in using ordinary trace minerals, which are most often metal salts.

The combination of water, ethyl alcohol, molasses, chelated minerals and a vitamin mix is thus unique and heretofore unknown in the prior art. As the main object of the present invention is to quickly and efficiently return livestock after transport to a normal condition, each of the ingredients has been selected to operate as quickly and efficiently as possible. The ethyl alcohol has been chosen to provide an immediate energy source which will help livestock to get to the feed bunk and begin eating in a short period of time. The chelated minerals may be absorbed into the livestock's blood stream with greater efficiency than was previously possible in using trace minerals, thus reducing the amount of minerals which must be ingested to replace those minerals lost by the livestock. Additionally, the molasses provides an ideal carrying agent for suspending all of the ingredients of the present product such that ingredients will not separate out during the time the product is not being used.

Shown below is one preferred embodiment of the product of the present invention. The water, ethyl alcohol, vitamin mixes and cane molasses have been previously discussed, and the chelated minerals are represented by the "Nutra Sol Base" and "Mg/K Base".

TABLE 1

| INGREDIENT | WEIGHT (LBS.) | PERCENT BY WEIGHT |
| --- | --- | --- |
| H$_2$O | 635.49 | 31.77 |
| Ethyl Alcohol (190 proof) | 240.00 | 12.00 |
| Clay | 30.00 | 1.50 |
| Salt | 50.00 | 2.50 |
| Nutra Sol Base (Cu, Zn, Mn) | 40.00 | 2.00 |
| Mg/K Base | 35.00 | 1.75 |
| B Complex | .42 | .02 |
| Vitamins A, D, E | 3.31 | .17 |
| Cane Molasses | 839.98 | 42.00 |
| Ammonium Polyphosphate | 124.00 | 6.20 |

TABLE 1-continued

| INGREDIENT | WEIGHT (LBS.) | PERCENT BY WEIGHT |
|---|---|---|
| Selenium | 1.77 | .09 |
| Vitamin E | .02 | .00 |

"Nutra Sol Base" and "Mg/K Base" are chelated mineral products produced by Albion Laboratories of Clearfield, Utah, providing, respectively, amino acid chelates of copper, zinc and manganese and amino acid chelates of magnesium and potassium. Any replacement source of amino acid chelates may be substituted, however.

Clay is provided in the product to act as a further suspension agent to assist the molasses in keeping all of the ingredients of the product homogeneously mixed. Both salt and ammonium polyphosphate have been added in accordance with Alcohol, Tobacco and Firearms Department regulations, which do not allow simple combination of molasses and ethyl alcohol. Additionally, the salt and ammonium polyphosphate provide nitrogen and phosphorous to assist in replacing those minerals. It is to be understood that any similar provider of nitrogen and/or phosphorous may be substituted for the salt or ammonium polyphosphate, in accordance with Alcohol, Tobacco and Firearms regulations.

Finally, selenium, which is not a chelated mineral, is added to provide additional minerals for livestock. The amount of selenium present in the product is limited through regulation and thus may be changed or even eliminated depending on the use for which the product is intended.

It is preferred that the product of the present invention be prepared by mixing the ethyl alcohol, clay suspension agent, and water for a total of approximately 5 minutes. The remaining ingredients are then added one at a time and all 12 ingredients are then mixed for a total of approximately 15 minutes. During this process, it is contemplated that the mixer be rotated continually at approximately 1,000 rpm. Most of the ingredients are put into the mixer at a fairly fast pace, except the molasses which flows into the mixer more slowly than the other parts of the formula. It is estimated that total time from start to finish for the product to attain homogeneity is approximately 30 minutes. The synergistic result of this method is that the product may be used to significantly reduce livestock stress during weaning and adapting to new feedlot and feeding environments. This alleviation of the stress results in animals going on feed faster, improved performance, less repeat treatments and reduced death loss.

An important goal of the present invention is to allow a user of the invention to administer a dosage of the product and have a favorable response from livestock within 96 hours following the administration. While it is contemplated that the product of the present invention may be used as a feed supplement or as a top dressing for feed, it is preferred that the present invention be administered directly to livestock as a drench. In the preferred embodiment, a dosage of the product would be placed into a throat injecting device, and administered in the following manner. The livestock's mouth is opened, and the throat injection apparatus is inserted into the animal's mouth with the injection opening pointing down the animal's throat. The product of the present invention is then dispensed into the animal's throat and thus directly into the animal's digestive tract. No actual injection of the product, meaning penetration of flesh, takes place. This is the preferred method of application, as the dosage of the product may be precisely controlled and the animal may be treated without having to wait for the animal to feed. One of the disadvantages found in the prior art is that many of the products of the prior art designed to alleviate stress rely on the animal to feed to receive a dosage of the prior art product. However, one of the main problems encountered in transporting animals is loss of the animal's appetite. Therefore, if administration of treatment is intended to restore the animal's appetite, but treatment of the animal is accomplished by waiting for the animal to feed, it would seem that the intended treatment to induce appetite is administered too late, after the animal has already regained its appetite. As it is important to get the animal to the feed bunk as soon as possible after transport, administration of a stress-relieving treatment by the method described above in connection with the present invention is preferable.

An additional feature of the present invention is that it may be administered using presently available drenching equipment, as the present product is in liquid form.

It is to be understood that the present invention is not only designed to alleviate stress resulting from shipping and handling of livestock, but also stress resulting from any other operation involving livestock, such as dehorning, castration, or any other similar traumatic experience.

The present invention thus provides a substantial improvement over the prior art. The use of molasses and ethyl alcohol in combination results in a rich and efficient energy source being introduced into the livestock's system. Furthermore, the use of chelated minerals in connection with the above ingredients leads to a much higher degree of bioavailability of minerals to the animal's system, thus resulting in a much quicker and more efficient absorption of minerals. The vitamin mix meets and in some cases exceeds the animals needs, and as has been shown, increased levels vitamins can contribute to stimulation of the immune system. The increased bioavailability of minerals due to the use of chelated minerals also contributes to proper immune system function. In combination, then, the above ingredients can significantly reduce stress in 24 to 96 hours following administration thereof, thus resulting in animals going on feed faster, improved performance, less repeat treatments and reduced death loss.

It is to be understood that numerous modifications and substitutions may be made to the present invention. For example, various kinds of molasses may be used, and additional chelated minerals may be added to the product of the present invention, such as ion, phosphorous, or cobalt. It is intended that the scope of the invention be broad enough to cover any such substitutions, the scope of the invention defined and set forth in the claims which shall follow.

There has thus been described and presented an invention which accomplishes at least all of the stated objectives.

We claim:

1. A method of treating livestock for adaptation stress, said method comprising, providing molasses, water, ethyl alcohol, minerals including at least magnesium and potassium, said minerals chelated with an amino acid and a vitamin mix;

mixing said ethyl alcohol and said water;

adding each of the remaining ingredients to the mixture of said ethyl alcohol and said water;

mixing until homogeneous to provide a liquid treatment for livestock adaptation stress; and administering said liquid treatment to said livestock.

2. The method of claim 1 further comprising the step of providing a liquid suspension agent and ammonium polyphosphate and said mixing step further includes mixing said liquid suspension agent with said ethyl alcohol and said water and said adding step further includes adding said ammonium polyphosphate with said remaining ingredients.

3. The method of claim 2 wherein said ethyl alcohol, said water and said liquid suspension agent are mixed for from two to eight minutes.

4. The method of claim 3 wherein the remaining ingredients and ammonium polyphosphate are added separately to the mixture of claim 3, the resulting combination being mixed for from ten to twenty minutes until homogenous.

5. A product for treating livestock comprising,
   a generally homogenous mixture of at least the following ingredients: water, ethyl alcohol, molasses, minerals including at least magnesium and potassium, said minerals chelated with an amino acid and a vitamin mix,
   said water comprising about 10%–50% of said mixture by weight,
   said ethyl alcohol comprising about 3%–25% of said mixture by weight,
   said molasses comprising about 20%–65% of said mixture by weight,
   said chelated minerals comprising about 1%–10% of said mixture by weight, and
   said vitamin mix comprising about 0.01% to 2% of said mixture by weight.

6. The product of claim 5 further comprising a liquid suspension agent comprising about 0.5%–5% of said mixture by weight.

7. The product of claim 5 further comprising salt and ammonium polyphosphate, said salt comprising about 1%–10% of said mixture by weight, said ammonium polyphosphate comprising about 3%–15% of said mixture by weight.

8. The product of claim 5 wherein said molasses comprises black strap cane molasses.

9. The product of claim 5 wherein said chelated minerals comprise amino acid chelates of minerals selected from, but not limited to, the following minerals: zinc, copper, magnesium, potassium, manganese, iron, phosphorus and cobalt.

10. The product of claim 5 wherein said product is mixed until substantially complete homogeneity is achieved.

11. A method of treating livestock to reduce livestock adaptation stress, said method comprising:
    administering to livestock following arrival of said livestock in a new lot a treatment product in an amount to reduce lot adaptation stress, said product comprising as major ingredients molasses, water, ethyl alcohol and minerals including at least magnesium and potassium, which minerals are chelated with an amino acid, and as minor ingredients, in less quantity than said major ingredients at least a vitamin mix, said water and said ethyl alcohol mixed together, the other ingredients added to said water and said ethyl alcohol mixture, the resulting mixture being mixed until homogenous.

* * * * *